United States Patent
i Blasco et al.

(10) Patent No.: US 7,105,664 B2
(45) Date of Patent: Sep. 12, 2006

(54) 5-HALOGEN-6-PHENYL-7-FLUOROALKYLAMINO-TRIAZOLOPYRIMIDINES AS FUNGICIDES

(75) Inventors: Jordi Tormo i Blasco, Limburgerhof (DE); Eberhard Ammermann, Heppenheim (DE); Klaus-Jürgen Pees, Mainz (DE); Guido Albert, Hackenheim (DE); Annerose Rehnig, Ingelheim (DE); Debra Search, New Egypt, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 206 days.

(21) Appl. No.: 10/474,460

(22) PCT Filed: Apr. 6, 2002

(86) PCT No.: PCT/EP02/03829

§ 371 (c)(1),
(2), (4) Date: Oct. 8, 2003

(87) PCT Pub. No.: WO02/083676

PCT Pub. Date: Oct. 24, 2002

(65) Prior Publication Data

US 2004/0127509 A1   Jul. 1, 2004

(30) Foreign Application Priority Data

Apr. 11, 2001 (EP) ................... 01109011

(51) Int. Cl.
C07D 487/04 (2006.01)
A01N 43/90 (2006.01)
(52) U.S. Cl. ................... 544/263; 514/259.31
(58) Field of Classification Search ........... 514/259.31; 544/263
See application file for complete search history.

(56) References Cited

U.S. PATENT DOCUMENTS 4,567,263 A    1/1986  Eicken et al.
2002/0068744 A1*  6/2002  Schmitt et al. ........ 514/259.31

FOREIGN PATENT DOCUMENTS

EP   550 113    7/1993
WO   98/46607   10/1998
WO   98/46608   10/1998

* cited by examiner

*Primary Examiner*—Thomas C. McKenzie
(74) *Attorney, Agent, or Firm*—Novak Druce & Quigg, LLP; Jason D. Voight

(57) ABSTRACT

5-Halogen-6-phenyl-7-fluoroalkylamino-triazolopyrimidines of formula I: (I) in which $R^1$ is hydrogen, fluoro, alkyl, alkenyl, alkynyl, alkadienyl, where the carbon chains of these radicals may be unsubstituted or substituted as defined in the description; $R^2$ is hydrogen, alkyl, alkenyl, alkynyl, alkadienyl, where these radicals may be unsubstituted or substituted; $R^3$ is fluoroalkyl or fluoroalkenyl; X is halogen; n is 0 or an integer from 1 to 4; L each independently is halogen, nitro, alkyl, haloalkyl, alkoxy or haloalkoxy. Processes for their preparation, compositions containing them and to their use for combating phytopathogenic fungi.

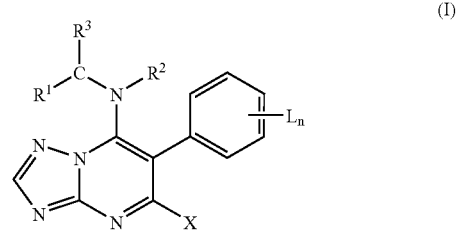

(I)

15 Claims, No Drawings

5-HALOGEN-6-PHENYL-7-FLUOROALKYLAMINO-TRIAZOLOPYRIMIDINES AS FUNGICIDES

The present Invention relates to 5-halogen-6-phenyl-7-fluoroalkylamino-triazolopyrimidines of formula I

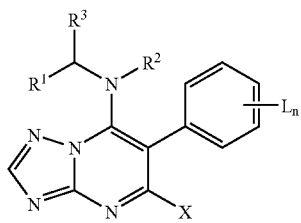

in which
$R^1$ is hydrogen, fluoro, $C_1$–$C_{10}$-alkyl, $C_2$–$C_{10}$-alkenyl, $C_2$–$C_{10}$-alkynyl, $C_2$–$C_{10}$-alkadienyl,
where the carbon chains of these radicals may be unsubstituted or partially or fully halogenated or may carry one to three groups $R^a$,
$R^a$ is cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy, which may be halogenated;
$R^2$ is hydrogen, $C_1$–$C_{10}$-alkyl, $C_2$–$C_{10}$-alkenyl, $C_2$–$C_{10}$-alkynyl, $C_2$–$C_{10}$-alkadienyl, where these radicals may be unsubstituted or partially or fully halogenated or may carry one to three groups $R^a$,
$R^3$ is $C_2$–$C_8$-fluoroalkyl or $C_2$–$C_8$-fluoroalkenyl;
X is halogen;
n is 0 or an integer from 1 to 4;
L each independently is halogen, nitro, $C_1$–$C_{10}$-alkyl, $C_1$–$C_6$-haloalkyl, $C_1$–$C_{10}$-alkoxy or $C_1$–$C_6$-haloalkoxy.

Moreover, the invention relates to processes for their preparation, compositions containing them and to their use for combating phytopathogenic fungi.

EP-A 071 792 discloses 6-phenyl-7-amino-triazolopyrimidines where the 5-position is substituted by hydrogen or alkyl or aryl groups.

EP-A 550-113 relates to 5-H— and 5-halogen-6-phenyl-7-amino-triazolopyrimidines where the 7-amino group is further substituted.

WO-A 98/46607 discloses funcidal triazolopyrimidines, which are substituted in the 6-position by a 2,4,6-trifluorophenyl group.

WO-A 98/46608 discloses funcidal triazolopyrimidines, which are substituted in the 7-position by a fluoroalkylamino group.

The compounds disclosed in the documents discussed above are said to be active against various phytopathogenic fungi.

It is an object of the present invention to provide compounds having improved fungicidal activity.

We have found that this object is achieved by the compounds defined at the outset. Furthermore, we have found processes for their preparation, compositions comprising them and methods for controlling phytopathogenic fungi using the compounds I.

The compounds of the formula I differ from the compounds known from closest prior art, which is WO-A 98/46608, in the specific definition of the 7-fluoralkylamino group, wherein the carbon chain in $R^3$ consists of at least two carbon atoms.

A 4- to 6-membered heterocyclic group may be any heterocyclic group with 4 to 6 ring atoms, interrupted by one or more heteroatoms selected from sulfur, nitrogen, and oxygen, preferably oxygen. A halogen atom suitable denotes a fluorine, chlorine or bromine atom.

The present invention further provides a process for the preparation of compounds of formula I as defined above which comprises treating a 5,7-dihalo compound of formula II in which X is halogen with an amine of formula III

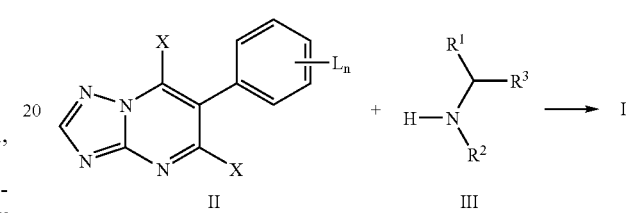

The reaction between the 5,7-dihalo compound II and the amine of formula III can be carried out under conditions known from WO-A 98/46608.

The reaction is preferably carried out in the presence of a solvent. Suitable solvents include ethers, such as dioxane, diethyl ether and, especially, tetrahydrofuran, halogenated hydrocarbons such as dichloromethane and aromatic hydrocarbons, for example toluene.

The reaction is suitably carried out at a temperature in the range from 0° C. to 70° C., the preferred reaction temperature being from 10° C. to 35° C.

It is also preferred that the reaction is carried out in the presence of a base. Suitable bases include tertiary amines, such as triethylamine, and inorganic bases, such as potassium carbonate or sodium carbonate. Alternatively, an excess of the compound of formula III may serve as a base.

In a further embodiment of-the invention the amine III is, activated by complexation with a free or complexed metal atom, such as lithium, sodium or copper, and the reaction of II is carried out with the complexed amine III'. In formula III' M denotes a free or complexed metal atom. The reaction conditions are in general similar as mentioned above.

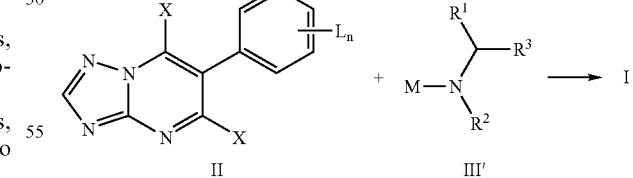

The reaction mixtures are worked up in a customary manner, for example by mixing with water, phase separation and, if required, chromatographic purification of the crude products. Some of the end products are obtained in the form of colorless or slightly brownish, viscous oils, which are purified or freed from volatile components under reduced pressure and at moderately elevated temperatures. If the end products are obtained as solids, purification can also be carried out by recrystallization or digestion.

Compounds of formula II are known in the art and can be obtained by synthesis routes disclosed in EP-A 550 113 and WO-A 98/46608.

If individual compounds I are not obtainable by the routes described above, they can be prepared by derivatization of other compounds I.

In the symbol definitions given in the formulae above, collective terms were used which generally represent the following substituents:

halogen: fluorine, chlorine, bromine and iodine;

$C_1$–$C_{10}$-alkyl and the alkyl moieties of $C_1$–$C_{10}$-haloalkyl: saturated, straight-chain or branched hydrocarbon radicals having 1 to 10, especially 1 to 6 carbon atoms, for example $C_1$–$C_4$-alkyl as mentioned above or pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3- dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_1$–$C_6$-haloalkyl and the haloalkyl moieties of $C_1$–$C_6$-haloalkoxy: straight-chain or branched alkyl groups having 1 to 6, preferably 1 to 4 carbon atoms (as mentioned above), where the hydrogen atoms in these groups may be partially or fully replaced by halogen atoms as mentioned above, for example-$C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_1$–$C_6$-fluoroalkyl and the fluoroalkyl moieties of $C_1$–$C_6$-fluoroalkoxy: straight-chain or branched alkyl groups having 1 to 6, preferably 1 to 4 carbon atoms (as mentioned above), where the hydrogen atoms in these groups may be partially or fully replaced by fluorine atoms as mentioned above, for example $C_1$–$C_2$-fluoroalkyl, such as fluoromethyl, difluoromethyl, trifluoromethyl, 1-fluoroethyl, 2-fluoroethyl, 2,2-difluoroethyl, 2,2,2-trifluoroethyl and pentafluoroethyl;

$C_2$–$C_{10}$-alkenyl: unsaturated, straight-chain or branched hydrocarbon radicals having 2 to 10, especially 3 to 6 carbon atoms and a double bond in any position, for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl;

$C_2$–$C_{10}$-alkynyl: straight-chain or branched hydrocarbon radicals having 2 to 10, especially 2 to 4 carbon atoms and a triple bond in any position, for example ethynyl, 1-propynyl, 2-propynyl, 1-butynyl, 2-butynyl, 3-butynyl and 1-methyl-2-propynyl.

With respect to their intended use, preference is given to triazolopyrimidines of the formula I having the following substituents, where the preference is valid in each case on its own or in combination:

The particularly preferred embodiments of the intermediates with respect to the variables correspond to those of the radicals X, $R^1$ and $R^2$ of formula I.

A preferred alkyl moiety is an ethyl or especially a methyl group.

A preferred haloalkyl moiety is the 2,2,2-trifluoroethyl or 1,1,1-trifluoroprop-2-yl group;

A preferred alkenyl moiety is allyl or especially a 2-methylallyl group.

Likewise, preference is given to compounds of formula I wherein $R^1$ is not hydrogen.

Compounds of formula I are preferred in which $R^1$ represents fluorine or straight-chained or branched $C_1$–$C_{10}$-alkyl, in particular branched $C_{3-10}$-alkyl.

Furthermore, particular preference is-given to compounds I in which $R^1$ is fluorine.

Particular preference is given to compounds I in which $R^2$ represents a hydrogen atom, a $C_1$–$C_{10}$-alkyl or a $C_1$–$C_{10}$-haloalkyl group, in particular a hydrogen atom.

Besides, particular preference is given to compounds I in which $R^2$ is hydrogen.

Moreover, particular preference is given to compounds I in which $R^2$ is methyl.

Particular preference is given to compounds of formula I in which $R^3$ denotes a group A

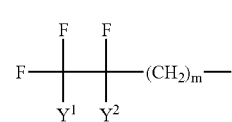

wherein $Y^1$ is hydrogen, fluoro or $C_1$–$C_6$-fluoroalkyl, $Y^2$ is hydrogen or fluoro, or $Y^1$ and $Y^2$ taken together form a double bond; and m is 0 or 1.

If $R^3$ denotes a $C_1$–$C_{10}$-haloalkyl group, preferably a polyfluorinated alkyl group, in particular a 2,2,2-trifluoroethyl, a 2-(1,1,1-trifluoropropyl) or a 2-(1,1,1-trifluorobutyl) group, $R^2$ preferably represents a hydrogen atom.

$L_n$ preferably is halogen or $C_1$–$C_6$-alkoxy. A preferred embodiment are compounds of formula I in which.

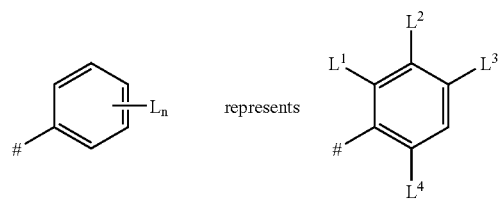

wherein # denotes the link to the triazolopyrimidine moiety, $L^1$ through $L^4$ each independently represent hydrogen, especially fluorine, chlorine, methyl or methoxy, in particular wherein $L^1$ is fluoro, $L^2$ is hydrogen or fluoro, $L^3$ is hydrogen or fluoro or methoxy and $L^4$ denotes hydrogen, fluoro chloro or methyl.

Moreover, particular preference is given to compounds of the formula I in which n is 2 or 3. Most preferred $L^4$ is not hydrogen.

Furthermore, particular preference is given to compounds of formula IA in which $R^1$ to $R^3$ have the meaninng as defined in formula I and $L^1$ to $L^4$ have the meanings given above.

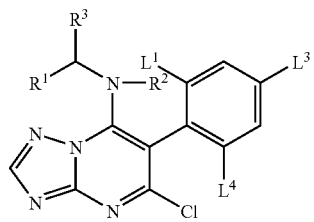

IA

Particular preference is given to compounds of formula IA in which $L^1$ denotes halogen and $L^3$ and $L^4$ each independently represent hydrogen, halogen or $C_1$–$C_4$-alkoxy.

Most preferred are compounds of formula IA in which $L^1$ is fluoro, $L^3$ is hydrogen and $L^4$ is chloro.

Particularly preference is given to compounds of formula IA wherein $R^2$ is hydrogen, $L^1$ and $L^4$ independently represent fluorine or chlorine atoms, and $L^3$ denotes hydrogen, fluorine, chlorine or methoxy.

Included in the scope of the present invention are (R) and (S) isomers of compounds of general formula I having a chiral center and the racemates thereof, and salts, N-oxides and acid addition compounds.

With respect to their use, particular preference is given to the compounds I compiled in the tables below. The groups mentioned in the table for a substituent are furthermore for their part, independently of the combination in which they are mentioned, a particularly preferred embodiment of the respective substituents.

Table 1

Compounds of the formula IA, in which $L^1$ is fluoro, $L^3$ is hydrogen, $L^4$ is chloro and $R^1$, $R^2$ and $R^3$ correspond to one row in Table A Table 2

Compounds of the formula IA, in which $L^1$ and $L^4$ each are fluoro, $L^3$ is hydrogen and $R^1$, $R^2$ and $R^3$ correspond to one row in Table A Table 3

Compounds of the formula IA, in which $L^1$ and $L^4$ each are chloro, $L^3$ is hydrogen and $R^1$, $R^2$ and $R^3$ correspond to one row in Table A Table 4

Compounds of the formula IA, in which $L^1$ is methyl, $L^3$ is hydrogen, $L^4$ is fluoro and $R^1$, $R^2$ and $R^3$ correspond to one row in Table A Table 5

Compounds of the formula IA, in which $L^1$, $L^3$ and $L^4$ each are fluoro and $R^1$, $R^2$ and $R^3$ correspond to one row in Table A Table 6

Compounds of the formula IA, in which $L^1$ and $L^4$ each are fluoro, $L^3$ is methoxy and $R^1$, $R^2$ and $R^3$ correspond to one row in Table A Table 7

Compounds of the formula IA, in which $L^1$ and $L^3$ are each hydrogen, $L^4$ is fluoro and $R^1$, $R^2$ and $R^3$ correspond to one row in Table A Table 8

Compounds of the formula IA, in which $L^1$ and $L^3$ are each hydrogen, $L^4$ is chloro and $R^1$, $R^2$ and $R^3$ correspond to one row in Table A Table 9

Compounds of the formula I, in which $L_n$ is 2-F-5-$NO_2$, X is chloro and $R^1$, $R^2$ and $R^3$ correspond to one row in Table A Table 10

Compounds of the formula I, in which $L_n$ is pentafluoro, X is chloro and $R^1$, $R^2$ and $R^3$ correspond to one row in Table A

TABLE A

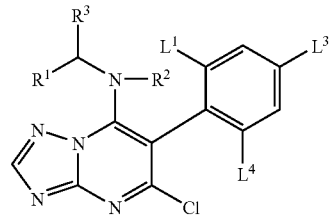

IA

| No. | $R^1$ | $R^2$ | $R^3$ |
|---|---|---|---|
| A-1 | F | H | $CH_2CF_3$ |
| A-2 | F | $CH_3$ | $CH_2CF_3$ |
| A-3 | F | $CH_2CH_3$ | $CH_2CF_3$ |
| A-4 | F | $CH_2CH_2CH_3$ | $CH_2CF_3$ |
| A-5 | F | H | $CH_2C(CF_3)=CH_2$ |
| A-6 | F | $CH_3$ | $CH_2C(CF_3)=CH_2$ |
| A-7 | F | $CH_2CH_3$ | $CH_2C(CF_3)=CH_2$ |
| A-8 | F | H | $CH_2C(CH_3)=CF_2$ |
| A-9 | F | $CH_3$ | $CH_2C(CH_3)=CF_2$ |
| A-10 | F | $CH_2CH_3$ | $CH_2C(CH_3)=CF_2$ |
| A-11 | F | H | $CH_2CF=CH_2$ |
| A-12 | F | $CH_3$ | $CH_2CF=CH_2$ |
| A-13 | F | $CH_2CH_3$ | $CH_2CF=CH_2$ |
| A-14 | F | H | $CH_2CH=CF_2$ |
| A-15 | F | $CH_3$ | $CH_2CH=CF_2$ |
| A-16 | F | $CH_2CH_3$ | $CH_2CH=CF_2$ |
| A-17 | H | H | $CF_2CF_3$ |
| A-18 | H | $CH_3$ | $CF_2CF_3$ |
| A-19 | H | $CH_2CH_3$ | $CF_2CF_3$ |
| A-20 | H | $CH_2CH_2CH_3$ | $CF_2CF_3$ |
| A-21 | H | H | $CHFCF_3$ |
| A-22 | H | $CH_3$ | $CHFCF_3$ |
| A-23 | H | $CH_2CH_3$ | $CHFCF_3$ |
| A-24 | H | $CH_2CH_2CH_3$ | $CHFCF_3$ |
| A-25 | H | H | $CH_2CF_2CF_3$ |
| A-26 | H | $CH_3$ | $CH_2CF_2CF_3$ |
| A-27 | H | $CH_2CH_3$ | $CH_2CF_2CF_3$ |
| A-28 | H | $CH_2CH_2CH_3$ | $CH_2CF_2CF_3$ |
| A-29 | H | H | $CH(CH_3)CH_2CF_3$ |
| A-30 | H | $CH_3$ | $CH(CH_3)CH_2CF_3$ |
| A-31 | H | $CH_2CH_3$ | $CH(CH_3)CH_2CF_3$ |
| A-32 | H | $CH_2CH_2CH_3$ | $CH(CH_3)CH_2CF_3$ |
| A-33 | H | H | $CH_2CH=CF_2$ |
| A-34 | H | $CH_3$ | $CH_2CH=CF_2$ |
| A-35 | H | $CH_2CH_3$ | $CH_2CH=CF_2$ |
| A-36 | H | $CH_2CH_2CH_3$ | $CH_2CH=CF_2$ |
| A-37 | H | H | $CH_2CF=CF_2$ |
| A-38 | H | $CH_3$ | $CH_2CF=CF_2$ |
| A-39 | H | $CH_2CH_3$ | $CH_2CF=CF_2$ |
| A-40 | H | $CH_2CH_2CH_3$ | $CH_2CF=CF_2$ |

The compounds I are suitable as fungicides. They have outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

*Alternaria* species on vegetables and fruit,
*Botrytis cinerea* (gray mold) on strawberries, vegetables, ornamentals and grapevines,
*Cercospora arachidicola* on peanuts,
*Erysiphe cichoracearum* and *Sphaerotheca fuliginea* on cucurbits,
*Blumeria graminis* (powdery mildew) on cereals,
*Fusarium* and *Verticillium* species on various plants,
*Helminthosporium* species on cereals,
*Mycosphaerella* species on bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and lawns,
*Septoria* species in cereals,
*Uncinula necator* on grapevines,
*Ustilago* species on cereals and sugar cane, and
*Venturia* species (scab) on apples and pears.

Moreover, the compounds I are suitable for controlling harmful fungi such as *Paecilomyces variotii* in the protection of materials (e.g. wood, paper, paint dispersions, fibers and tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

The compounds I can be converted into the customary formulations, e.g. solutions, emulsions, suspensions, dusts, powders, pastes and granules. The use form depends on the particular purpose; in any case, it should guarantee a fine and uniform distribution of the compound according to the invention.

The formulations are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly-disperse silica, silicates); emulsifiers such as non-ionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylaryl-sulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalene-sulfonic acid with phenol or formaldehyde, polyoxyethylene octylphenyl ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Substances which are suitable for the preparation of directly sprayable solutions, emulsions, pastes or oil dispersions-are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for scattering and dusts can be prepared by mixing or concomitantly grinding the active substances with a solid carrier.

Granules, e.g. coated granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol. of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a-solution which is suitable for use in the form of microdrops-(comprises 90% by weight of active ingredient).

VII. 20 parts by weight-of a compound according to the invention are dissolved in a mixture composed of 40 parts by weight of cyclohexanone, 30 parts by-weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts-by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, scattering or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides, or bactericides may be added to the active ingredients, if appropriate also only immediately prior to use (tank mix). These agents can be admixed with the agents according to the invention in a weight ratio of 1:10 to 10:1.

In the use form as fungicides, the compositions according to the invention can also be present together with other active ingredients, e.g. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides, together with which the compounds according to the invention can be used, is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro(l-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-l-[bis(dime-thylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfo-diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methyl-furan-3-carboxanilide, 2,5-dimethylfuran-3-carboxanilide, 2,4,5-trimethylfuran-3-carboxanilide, N-cyclohexyl- 2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-l-(2,2,2-trichloroethyl)formamide, 1-(3,4-dichloroanilino)-1- formylamino-2,2,2-trichloroethane; 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethyl-morpholine, N-[3-(p-tert-butylphenyl)-2-methylpropyl]-piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolyl-urea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)-oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurines such as azoxystrobin, kresoxim methyl, methyl-E-methoxyimino-[α-(2-phenoxyphenyl)]-acetamide, methyl E-methoxyimino-[α-(2,5-dimethylphenoxy)-o-tolyl]acetamide, picoxystrobin, pyraclostrobin, trifloxystrobin, anilinopyrimidines such as N-(4,6-dimethylpyrimidin-2-yl)aniline, N-[4-methyl-6-(1-propynyl)pyrimidin-2-yl]-aniline, N-[4-methyl-6-cyclopropylpyrimidin-2-yl]aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxyphenyl)acryloylmorpholine, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-amino- butyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino)acetamide, 1-[2-(2,4-dichloro-phenyl)pentyl]-1H-1,2,4-triazole, 2,4-di-fluoro-α-(1H-1,2,4-triazolyl-l-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

SYNTHESIS EXAMPLES

With due modification of the starting compounds, the protocols shown in the synthesis examples below were used for obtaining further compounds I. The resulting compounds, together with physical data, are listed in the Table which follows.

Example 1

Preparation of 5-chloro-6-(2-chloro-6-fluorophenyl)-7-(1,1,1-trifluorobut-4-yl)-amino-[1,2,4]-triazolo(1,5-α]pyrimidine [I-9]

A solution of 1.5 mmol 1,1,1-trifluorobutane-4-amine, 1.5 mmol triethylamine in 10 ml dichloromethane is added to a solution of 1.5 mmol 5,7-dichloro-6-(2-chloro-6-fluorophenyl)-[1,2,4]-triazolo[1,5-α]pyrimidine [cf. EP-A 550 113] in 20 ml dichloromethane. The combined solution was stirred for about 16 hours at 20 to 25° C. and subsequently washed with diluted (5%) hydrochloric acid. The organic phase was separated, dried and filtered. Distillative removal of the solvent from the filtrate and chromatography over silica gel yielded 0.45 g of the title compound of mp. 115° C.

TABLE I

| No. | $R^1$ | $R^2$ | $R^3$ | $L_n$ | phys. data (m.p.[° C.]) |
|---|---|---|---|---|---|
| I-1 | H | H | CHFCF$_3$ | 2,4,6-F$_3$ | 189 |
| I-2 | H | H | CH$_2$CF=CF$_2$ | 2,4,6-F$_3$ | 137 |
| I-3 | H | H | C(CH$_3$)CH$_2$CF$_3$ | 2,4,6-F$_3$ | 143 |
| I-4 | F | H | CH$_2$CF$_3$ | F$_5$ | 200 |
| I-5 | H | H | CH$_2$CF$_3$ | 2,4,6-F$_3$ | 202 |
| I-6 | H | H | CF$_2$CF$_3$ | 2-Cl-6-F | 140 |
| I-7 | H | H | CH$_2$CF$_3$ | 2,6-F$_2$-4-OCH$_3$ | 161 |
| I-8 | H | H | CF$_2$CF$_2$CF$_3$ | 2-Cl-6-F | 182 |
| I-9 | H | H | CH$_2$CH$_2$CF$_3$ | 2-Cl-6-F | 115 |
| I-10 | H | H | CH$_2$CH$_2$CF$_3$ | 2,4,6-F$_3$ | 142 |
| I-11 | H | H | CH$_2$CF=CF$_2$ | 2,6-F$_2$ | 130 |
| I-12 | H | H | CH$_2$CF=CF$_2$ | 2-Cl | 129 |
| I-13 | H | H | CH$_2$CF=CF$_2$ | 2-F | 111 |
| I-14 | H | H | CH$_2$CF=CF$_2$ | 2-Cl-6-F | 107 |
| I-15 | H | H | CH$_2$CF=CF$_2$ | F$_5$ | 118 |
| I-16 | H | H | CHFCF$_3$ | 2-NO$_2$-5-F | syrup |
| I-17 | H | H | CHFCF$_3$ | 2-Cl-6-F | 199 |
| I-18 | H | H | CHFCF$_3$ | 2,6-F$_2$ | 80 |
| I-19 | H | H | CH$_2$CH$_2$CF$_3$ | 2-F | 81 |

EXAMPLES OF THE ACTION AGAINST HARMFUL FUNGI

The fungicidal-action of the compounds of the formula I was demonstrated by the following experiments:

The active compounds, separately or together, were formulated as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted with water to the desired concentration.

Use Example 1

Fungicidal control of apple scab
(*Venturia inequalis*)

Young apple seedlings of the cultivar "Common" were grown-in pots to the 4 to 5 leaf stage. These plants were sprayed to run-off with an aqueous suspension, containing the concentration of active ingredient mentioned below, prepared from a stock solution containing 5% of the active ingredient, 94% cyclohexanone and 1% emulsifier (Tween 20). After the plants had dried (3–5 h), they were inoculated with an aqueous spore suspension of *Venturia inequalis*. Then the trial plants were immediately transferred to a humid chamber with 22 to 24° C. and a relative humidity close to 100% and were cultivated there for 2 days. For a period of further 2 weeks a cultivation in a greenhouse followed at 21 to 23° C. and a relative humidity about 95%. Then the extent of fungal attack on the leaves was visually assessed as % diseased leaf area.

In this test, the plants which had been treated with 200 ppm of compounds I-1 to I-6 and I-8 to I-19 showed an infection of up to 15%, whereas the untreated plants were infected to 80%.

Use Example 2

Fungicidal control of early blight on tomatoes
(*Alternaria solani*)

Young tomato seedlings of the cultivar "Pixie II" were grown in pots to the 2 to 4 leaf stage. These plants were sprayed to run-off with an aqueous suspension, containing the concentration of active ingredient mentioned below, prepared from a stock solution containing 5% of the active ingredient, 94% cyclohexanone and 1% emulsifier (Tween 20). After the plants had dried (3–5 h), they were inoculated with an aqueous spore suspension of *Alternaria solani* containing $15 \times 10^3$ spores per ml. Then the trial plants were immediately transferred to a humid chamber with 22 to 24° C. and a relative humidity close to 100% for 36 h. For a period of further 2 to 3 days a cultivation in a greenhouse followed at 21 to 23° C. and a relative humidity about 95%. Then the extent of fungal attack on the leaves was visually assessed as % diseased leaf area.

In this test, the plants which had been treated with 200 ppm of compounds I-1 to I-7, I-9 to I-13, I-15, I-17, and I-18 showed an infection of up to 15%, whereas the untreated plants were infected to 90%.

Use Example 3

Fungicidal control of leaf spot on beets
(*Cercospora beticola*)

Young sugar beet seedlings of the cultivar "ACH-31" were grown in pots to the 2 to 4 leaf stage. These plants were sprayed to run-off with an aqueous suspension, containing the concentration of active ingredient mentioned below, prepared from a stock solution containing 5% of the active ingredient, 94% cyclohexanone and 1% emulsifier (Tween 20). After the plants had dried (3–5 h), they were inoculated with a spore suspension of *Cercospora beticola* in an aqueous solution of 0.5% gelatine. Then the trial plants were immediately transferred to a humid chamber with 18 to 23° C. and a relative humidity close to 100% and kept there for 5 days. For a period of further 10 to 14 days a cultivation in a greenhouse followed at 21 to 23° C. and a relative humidity about 95%. Then the extent of fungal attack on the leaves was visually assessed as % diseased leaf area.

In this test, the plants which had been treated with 200 ppm of compounds I-1 to I-4, I-6, I-8, and I-11 to I-19 showed an infection of up to 15%, whereas the untreated plants were infected to 85%.

Comparison Trials

Active compounds A to E known from WO-A 98/46607, WO-A 98/46608, and WO-A 99/48893 resp., were used as comparison compounds in the following comparison trials:

| No. | known from | $R^1$ | $L_n$ |
|---|---|---|---|
| A | WO-A 98/46607, Ex. 12 | H | 2,4,6-$F_3$ |
| B | WO-A 98/46608, Ex. 1 | H | 2-Cl-6-F |
| C | WO-A 98/46608, Ex. 5 | $CH_3$ | 2,6-$F_2$ |
| D | WO-A 99/48893, Ex. 6 | H | 2,6-$F_2$-4-$OCH_3$ |
| E | WO-A 99/48893, Ex. 7 | $CH_3$ | 2,6-$F_2$-4-$OCH_3$ |

Comparison Trial 1

Fungicidal control of rice blast caused by
*Pyricularia oryzae* (protective)

Leaves of pot-grown rice seedling of the variety "Tai-Nong 67" were sprayed to run-off with an aqueous suspension, containing the concentration of active ingredient as described below prepared from a stock solution containing 10 % of the active ingredient, 85 % cyclohexanone and 5 % emulsifier. The plants were allowed to air-dry. At the following day the plants were inoculated with an aqueous spore suspension of *Pyricularia oryzae* containing $1.0 \times 10^6$ spores/ml. Then the trial plants were immediately transferred to a humid chamber. After 6 days at 22–24° C. and a relative humidity close to 100% the extent of fungal attack on the leaves was visually assessed as % diseased leaf area.

In this trial, the plants which have been treated with 200 ppm of compounds I-1, I-2 and I-3, resp., showed an infection of 3%, whereas the plants treated with 200 ppm of comparison compounds A, B and C, resp., were infected to 60, 10, and 20%, resp., and the untreated plants were infected to 90%.

Comparison Trial 2

Control of powdery mildew on wheat caused by
*Blumeria graminis f.* sp. *tritici*

The first fully developed leaves of pot grown wheat of the variety "Kanzler" were sprayed to-run-off with an aqueous suspension, containing the concentration of active ingredient or their mixture mentioned in the table below, prepared from a stock solution containing 10% of the active ingredient, 85% cyclohexanone and 5% emulsifier. The next day the treated plants were inoculated with spores of *Blumeria graminis f.* sp. *tritici* (=syn. *Erysiphe garminis f.* sp. *tritici*) by shaking heavily infestated stock plants over the treated pots. After cultivation in the greenhouse for 7 days at 22–26° C. and a relative humidity between 60 to 90% the extent of fungal attack on-the leaves was visually assessed as % diseased leaf area.

In this trial, the plants which have been-treated with 200, and 50 ppm, resp. of compound I-7 showed an infection of 3, and 7%, whereas the plants treated with 200, and 50 ppm, resp. of comparison compounds D and E, resp., were infected (at 200 ppm) to 60 and 80%, resp., and (at 50 ppm) to 80%, and the untreated plants were infected to 100%.

What is claimed is:

1. 5-Halogen-6-phenyl-7-fluoroalkylamino-triazolo-pyrimidine of formula I

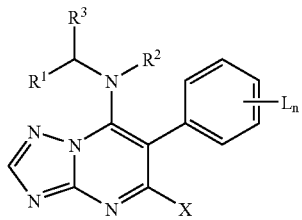

in which
R$^1$ is fluoro, C$_1$–C$_{10}$-alkyl, C$_2$–C$_{10}$-alkenyl, C$_2$–C$_{10}$-alkynyl, C$_2$–C$_{10}$-alkadienyl,
where the carbon chains of these radicals may be unsubstituted or partially or fully halogenated or may carry one to three groups R$^a$,
R$^a$ is cyano, nitro, hydroxyl, C$_1$–C$_6$-alkyl, C$_1$–C$_6$-haloalkyl, C$_1$–C$_6$-alkylcarbonyl, C$_3$–C$_6$-cycloalkyl, C$_1$–C$_6$-alkoxy, C$_1$–C$_6$-haloalkoxy, C$_1$–C$_6$-alkoxycarbonyl, C$_1$–C$_6$-alkylthio, C$_1$–C$_6$-alkylamino, di-C$_1$–C$_6$-alkylamino, C$_2$–C$_6$-alkenyl, C$_2$–C$_6$-alkenyloxy, C$_3$–C$_6$-alkynyloxy and C$_1$–C$_4$-alkylenedioxy, which may be halogenated;
R$^2$ is hydrogen, C$_1$–C$_{10}$-alkyl, C$_2$–C$_{10}$-alkenyl, C$_2$–C$_{10}$-alkynyl, C$_2$–C$_{10}$-alkadienyl, where these radicals may be unsubstituted or partially or fully halogenated or may carry one to three groups R$^a$,
R$^3$ is C$_2$–C$_8$-fluoroalkyl or C$_2$–C$_8$-fluoroalkenyl;
X is halogen;
n is 0 or an integer from 1 to 4;
L each independently is halogen, nitro, C$_1$–C$_{10}$-alkyl, C$_1$–C$_6$-haloalkyl, C$_1$–C$_{10}$-alkoxy or C$_1$–C$_6$-haloalkoxy.

2. Compounds according to claim 1 in which at least one L group is halogen.

3. Compounds according to claim 1 in which R$^1$ is fluorine or methyl.

4. Compounds according to claim 1 in which R$^2$ is hydrogen or C$_1$–C$_{10}$-alkyl.

5. A triazolopyrimidine compound of the formula I

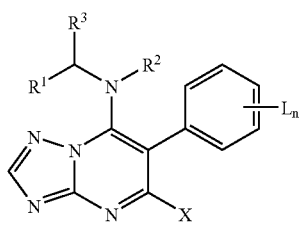

in which
R$^1$ is hydrogen, fluoro, C$_1$–C$_{10}$-alkyl, C$_2$–C$_{10}$-alkenyl, C$_2$–C$_{10}$-alkynyl, C$_2$–C$_{10}$-alkadienyl,
where the carbon chains of these radicals may be unsubstituted or partially or fully halogenated or may carry one to three groups R$^a$,
R$^a$ is cyano, nitro, hydroxyl, C$_1$–C$_6$-alkyl, C$_1$–C$_6$-haloalkyl, C$_1$–C$_6$-alkylcarbonyl, C$_3$–C$_6$-cycloalkyl, C$_1$–C$_6$-alkoxy, C$_1$–C$_6$-haloalkoxy, C$_1$–C$_6$-alkoxycarbonyl, C$_1$–C$_6$-alkylthio, C$_1$–C$_6$-alkylamino, di-C$_1$–C$_6$-alkylamino, C$_2$–C$_6$-alkenyl, C$_2$–C$_6$-alkenyloxy, C$_3$–C$_6$alkynyloxy and C$_1$–C$_4$alkylenedioxy, which may be halogenated;
R$^2$ is hydrogen, C$_1$–C$_{10}$alkyl, C$_2$–C$_{10}$-alkenyl, C$_2$C$_{10}$-alkynyl, C$_2$–C$_{10}$-alkadienyl, where these radicals may be unsubstituted or partially or fully halogenated or may carry one to three groups R$^a$,
R$^3$ is a group A

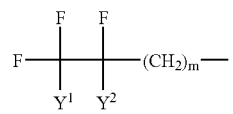

wherein
Y$^1$ is hydrogen, fluoro or C$_1$–C$_6$-fluoroalkyl,
Y$^2$ is hydrogen or fluoro, or
Y$^1$ and Y$^2$ taken together form a double bond; and
m is 0 or 1,
X is halogen;
n is 0 or an integer from 1 to 4; and
L each independently is halogen, nitro, C$_{-C10}$-alkyl, C$_1$–C$_6$-haloalkyl, C$_1$–C$_{10}$-alkoxy or C$_1$–C$_6$-haloalkoxy.

6. A compound according to claim 5 in which at least one L group is halogen.

7. A compound according to claim 5 in which R$^1$ is hydrogen, fluorine or methyl.

8. A compound according to claim 5 in which R$^2$ is hydrogen or C$_1$–C$_{10}$-alkyl.

9. A composition suitable for controlling phytopathogenic fungi, comprising a solid or liquid carrier and a triazolopyrimidine compound of the formula I

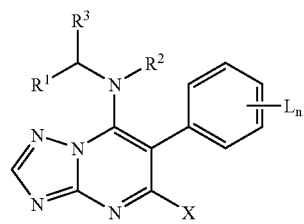

in which
R$^1$ is hydrogen, fluoro, C$_1$–C$_{10}$-alkyl, C$_2$–C$_{10}$-alkenyl, C$_2$–C$_{10}$-alkynyl, C$_2$–C$_{10}$-alkadienyl,
where the carbon chains of these radicals may be unsubstituted or partially or fully halogenated or may carry one to three groups R$^a$,
R$^a$ is cyano, nitro, hydroxyl, C$_1$–C$_6$-alkyl, C$_1$–C$_6$-haloalkyl, C$_1$–C$_6$-alkylcarbonyl, C$_3$–C$_6$-cycloalkyl, C$_1$–C$_6$-alkoxy, C$_1$–C$_6$-haloalkoxy, C$_1$–C$_6$-alkoxycarbonyl, C$_1$–C$_6$-alkylthio, C$_1$–C$_6$-alkylamino, di-C$_1$–C$_6$-alkylamino, C$_2$–C$_6$-alkenyl, C$_2$–C$_6$-alkenyloxy, C$_3$–C$_6$alkynyloxy and C$_1$–C$_4$alkylenedioxy, which may be halogenated;
R$^2$ is hydrogen, C$_1$–C$_{10}$-alkyl, C$_2$–C$_{10}$-alkenyl, C$_2$C$_{10}$-alkynyl, C$_2$–C$_{10}$-alkadienyl, where these radicals may be unsubstituted or partially or fully halogenated or may carry one to three groups R$^a$,
R$^3$ is C$_2$–C$_8$-fluoroalkyl or C$_2$–C$_8$-fluoroalkenyl;
X is halogen;
n is 0 or an integer from 1 to 4; and L each independently is halogen, nitro, $C_1$–$C_{10}$-alkyl, $C_1$–$C_6$-haloalkyl, $C_1$–$C_{10}$-alkoxy or $C_1$–$C_6$-haloalkoxy.

10. The composition according to claim 9 in which, in formula I, at leant one L group is halogen.

11. The composition according to claim 9 in which, in formula I, $R^1$ is hydrogen, fluorine or methyl.

12. The composition according to claim 9 in which, in formula I, $R^2$ is hydrogen or $C_1$–$C_{10}$-alkyl.

13. The composition according to claim 9 in which, in formula I, $R^3$ is a group A

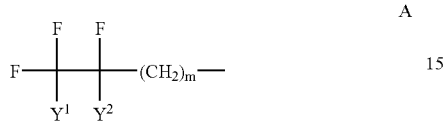

wherein
$Y^1$ is hydrogen, fluoro or $C_1$–$C_6$-fluoroalkyl,
$Y^2$ is hydrogen or fluoro, or
$Y^1$ and $Y^2$ taken together form a double bond; and
m is 0 or 1.

14. A method for controlling phytopathogenic fungi, which comprises treating the fungi or the materials, plants, the soil ot the seed to be protected against fungal attack with an effective amount of a compound of the formula I as claimed in claim 1.

15. A process for the preparation of compounds of formula I as defined in claim 1 which comprises reacting 5,7-dihalo-triazo-lopyrimidines of formula II

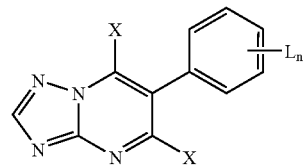

in which the variables have the meaning given in formula I with an amine of formula III

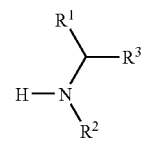

in which $R^1$, $R^2$ and $R^3$ are defined as in formula I to give compounds of formula I.

\* \* \* \* \*

UNITED STATES PATENT AND TRADEMARK OFFICE
CERTIFICATE OF CORRECTION

PATENT NO. : 7,105,664 B2
APPLICATION NO. : 10/474460
DATED : September 12, 2006
INVENTOR(S) : i Blasco et al.

It is certified that error appears in the above-identified patent and that said Letters Patent is hereby corrected as shown below:

Claim 5, column 16, indicated line 24: "$C\text{-}C_{10}\text{-alkyl}$" should read --$C\text{-}C_{10}\text{-alkyl}$--

Claim 10, column 17, indicated line 4: "at leant" should read --at least--

Claim 15, column 18, indicated line 3: "-triazo-lopyrimidines" should read -- -triazolopyrimidines--

Signed and Sealed this

Twenty-fourth Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 7,105,664 B2 Page 1 of 1
APPLICATION NO. : 10/474460
DATED : September 12, 2006
INVENTOR(S) : Tormo I. Blasco et al.

It is certified that error appears in the above-identified patent and that said Letters Patent is hereby corrected as shown below:

The Applicants' name indicated in subsection (12) on the face of the Patent, should read:
--Tormo i Blasco et al.-- rather than "i Blasco et al."

In Claim 5, col. 16, indicated line 24:
"$C\text{-}C_{10}$-alkyl" (*previously corrected to read '$C\text{-}C_{10}$-alkyl'*) should read
--$C_1\text{-}C_{10}$-alkyl--

Signed and Sealed this

Seventh Day of August, 2007

JON W. DUDAS
*Director of the United States Patent and Trademark Office*